United States Patent
Itoh et al.

(10) Patent No.: US 6,410,006 B2
(45) Date of Patent: *Jun. 25, 2002

(54) COMPOSITION FOR PROPHYLAXIS AND/OR TREATMENT OF DRY EYE SYNDROME COMPRISING VITAMIN D

(75) Inventors: Seiji Itoh, Mobara; Yasuo Ishii, Kawaguchi; Katsuhiko Mukai, Kashiwa; Kiyoshi Kita, Tokyo, all of (JP)

(73) Assignee: New Vision Co., Ltd., Tokyo (JP)

( * ) Notice: Subject to any disclaimer, the term of this patent is extended or adjusted under 35 U.S.C. 154(b) by 17 days.

This patent is subject to a terminal disclaimer.

(21) Appl. No.: 09/784,147

(22) Filed: Feb. 16, 2001

(Under 37 CFR 1.47)

Related U.S. Application Data

(63) Continuation of application No. 08/872,052, filed on Jun. 10, 1997, now abandoned.

(51) Int. Cl.⁷ ............................ A61K 31/74; A61F 2/00
(52) U.S. Cl. ...................... 424/78.04; 424/427
(58) Field of Search ............................ 424/427, 78.04; 514/912, 914

(56) References Cited

U.S. PATENT DOCUMENTS

| | | | |
|---|---|---|---|
| 4,335,120 A | 6/1982 | Holick et al. | 424/236 |
| 4,610,978 A | 9/1986 | Dikstein et al. | 514/46 |
| 4,923,699 A | 5/1990 | Kaufman | 424/427 |
| 5,254,538 A | 10/1993 | Holick et al. | 514/35 |
| 5,449,668 A | 9/1995 | Sestelo et al. | 514/167 |
| 5,876,709 A | 3/1999 | Itoh et al. | 424/78.04 |
| 6,187,331 B1 * | 2/2001 | Itoh et al. | 424/427 |

FOREIGN PATENT DOCUMENTS

| | | |
|---|---|---|
| EP | 0 412 641 | 2/1991 |
| EP | 862 916 | 9/1998 |
| JP | 63-145233 | 6/1988 |
| JP | 1249714 | 10/1989 |
| JP | 2-178218 | 7/1990 |
| JP | 4-43887 | 7/1992 |
| JP | 5-503922 | 6/1993 |
| JP | 5-320039 | 12/1993 |
| JP | 5-508655 | 12/1993 |
| WO | WO 96/29079 | 9/1996 |
| WO | WO 97/18817 | 5/1997 |
| WO | WO 98/51313 | 11/1998 |

OTHER PUBLICATIONS

Leslie Bendra Sabbagh, "Sunlight May Be Enemy of Healing Excimer PRK", Ocular Surgery News, vol. 9, No. 11, pp. 21–22, Jun. 1, 1991.

The Vitamins, pp 54–55, 104–115, 150–177, 206–221, Academic Press, Inc., 1992.

Dryeye Brochure, pp. 10–13, Nippon Hyoronsha, Japan, 1992.

Paul Riordan–Eva, "Preventive Ophthalmology", Appleton & Lange, pp. 388–395, 1993.

Ganka New Insight 5, pp. 132–143, Medical View–sha, Japan, 1995.

Olive Sheets et al., "The Effect of Ultra–Violet Rays on Rats, Deprived of Vitamine A in Their Diet", Scientific Proceedings, vol. 20, pp. 80–81, 1992.

G. F. Powers et al., "The Influence of Light and Darkness Upon the Development of Exerophthalmia in the Rat", Scientific Proceedings, vol. 20, pp. 81–85, 1992.

G. F. Powers et al., "The Influence of Radiant Energy Upon the Development of Xerophthalmia in Rats: A Remarkable Demonstration of the Beneficial Influence of Sunlight and Out–of–Door Air Upon the Organism", J. Biol. Chem., vol. 55, pp. 575–597, 1923.

\* cited by examiner

Primary Examiner—Thurman K. Page
Assistant Examiner—S. Howard
(74) Attorney, Agent, or Firm—Oblon, Spivak, McClelland, Maier & Neustadt, P.C.

(57) ABSTRACT

An ophthalmic composition for prophylaxis and/or treatment of keratoconjunctivitis sicca, which is locally administered to the eyes and which comprises, as an effective component, at least one member selected from the group consisting of vitamin D, active vitamin D, and active vitamin D analogues.

4 Claims, No Drawings

COMPOSITION FOR PROPHYLAXIS AND/OR TREATMENT OF DRY EYE SYNDROME COMPRISING VITAMIN D

This application is continuation of application Ser. No. 08/872,052, filed on Jun. 10, 1997, now abandoned.

TECHNICAL FIELD

The present invention relates to a composition for prophylaxis and/or treatment of keratoconjunctivitis sicca (dry eye syndrome) comprising vitamin D.

PRIOR ART

Keratoconjunctivitis sicca is called "dry eye" and is the focus of the discussion by ophthalmologists and others. "Ophthalmology New Insight 5" published by Medical Review Co., Ltd. describes corneal epithelial cells, vitamin A deficiency and keratoconjunctivitis sicca and refers to vitamin D in relation to epidermis. "Dry eye", a medical journal published by Nihon Hyoronsha presents widely keratoconjunctivitis sicca. According to them, they say that vitamin A deficiency is deeply involved in the disease of corneal conjunctival epithelium but vitamin D deficiency is not involved because there is not clinically present the disorder of corneal conjunctival epithelium in vitamin D deficiency.

The journal "Dry eye" classifies the dry eye syndrome into syndrome of decrease in the secretion of the lacrimal fluid and the disorder of keratoconjunctivitis sicca, and describes that they are due to decrease in the secretion of the lacrimal fluid and the disorder of cornea and conjunctiva. It is considered that keratoconjunctivitis sicca is caused by asthenopia which is caused by the reduction of the number of twinkling due to long time watching of video display terminals or televisions, or by dust in the windy day, ozone, nitrogen oxides, and the like. They say, for some reasons, cornification is caused in corneal epithelial cells or conjunctival Golbet cells; as a result, the lacrimal fluid cannot be kept in cornea or conjunctiva, or inflammatory reaction on cornea or conjunctiva extraordinarily reduces the mucin layer, the aqueous layer or the oil layer which constitutes the lacrimal fluid to cause keratoconjunctivitis sicca.

There have been proposed as therapy of keratoconjunctivitis sicca, the use of artificial lacrimal fluid, goggles for dry eye, herb medicine, dacryon plug and the like.

In general, the term "vitamin D" means vitamin $D_2$ (ergocalciferol) and vitamin $D_3$ (cholecalciferol) exhibiting a high anti-rachitis activity. It has been known that the vitamin D undergoes a change in its molecular structure (hydroxylation) in the liver and kidney and that it is thus converted into active vitamin D having high biological activities. It has also been supposed that vitamin D itself has, to some extent, certain biological activities.

Vitamin D's for therapy are administered to patients per oral route or by injection. It has been recognized that vitamin D's have not only a calcium-regulatory effect, but also other biological activities since the discovery of the active vitamin $D_3$, i.e., calcitriol (1α,25-dihydroxy cholecalciferol) as a derivative of cholecalciferol. Active vitamin D's include those carrying a hydroxyl group on one or both of the C1 position on the sterol A ring and the C25 position on the side chain, for example, calcitriol (1α,25-dihydroxy vitamin D), 1α,24-dihydroxy vitamin D, α-calcidol (1α-monohydroxy vitamin D), calcifedol (25-monohydroxy vitamin D), 1α,24, 25-trihydroxy vitamin D, 1β,25-dihydroxy vitamin D, 22-oxacalcitriol, and calcipotriol. Analogues thereof include dihydrotachysterol. The presence of active vitamin D receptors in cells has been discovered and there have been conducted studies on modification of cellular activities because of the ability of the active vitamin D's to control the production of various cytokines.

DISCLOSURE OF THE INVENTION

An object of the present invention is to provide an ophthalmic composition for prophylaxis and/or treatment of cornification of corneal or conjunctival cells which is caused by the reduction of the number of twinkling due to long time watching of the screen of televisions, or by dust in the windy day, ozone, nitrogen oxides, and the like, that is, to provide an ophthalmic composition for prophylaxis and/or treatment of keratoconjunctivitis sicca which is a syndrome of decrease in the secretion of the lacrimal fluid and disorders of conjunctiva and cornea.

The present invention is an ophthalmic composition for prophylaxis and/or treatment of keratoconjunctivitis sicca, which comprises, as an effective component, at least one member selected from the group consisting of vitamin D, active vitamin D, and active vitamin D analogues.

Particularly preferred vitamin D's used in the present invention include ergocalciferols and cholecalciferols, active vitamin D's include those carrying a hydroxyl group on one or both of the C1 position on the sterol A ring and the C25 position on the side chain, and vitamin D analogues include dihydrotachysterol.

The composition of the present invention does not use anti-rachitic activities of vitamin D but proceeds for conjunctival Golbet cells or corneal epithelial cells which have cornified or will cornify to perform normal differentiation. Namely, the composition administered is considered to accelerate differentiation of conjunctival Golbet cells or corneal epithelial cells to normalize the cells when the keratoconjunctivitis occurs. The activity of vitamin D administered to perform cellular differentiation is believed to be far lower than that of active form of vitamin D having biological activity.

BEST MODE FOR CARRYING OUT THE INVENTION

The composition of the present invention comprises at least one member selected from the group consisting of vitamin D, active vitamin D and active vitamin D analogues which are oil-soluble and formulated into eye drops for local use. The composition prevents and/or cures the cornification of conjunctival or corneal epithelial cells. Specific examples of the effective component of the composition of the present invention include ergocalciferols, cholecalciferols, calcitriol (1α, 25-dihydroxy vitamin D), 1α,24-dihydroxy vitamin D, a-calcidol (1α-monohydroxy vitamin D), calcifedol (25-monohydroxy vitamin D), 1α,24, 25-trihydroxy vitamin D, 1β, 25-dihydroxy vitamin D, 22-oxacalcitriol, calcipotriol and dihydrotachysterol.

The composition of the present invention can be formulated in various forms but most preferably in the form of eye drops. The concentration of the effective component in the composition of the present invention is suitably in the range of 0.001 to 100 μg/ml since the composition is locally administered. The effective component of the present invention, i.e., vitamin D, active vitamin D and active vitamin D analogues are not cytotoxic. Accordingly, the composition would not adversely affect conjunctival or corneal epithelial cells as long as the formulation is physiological.

When vitamin D or active vitamin D formulation is orally administered in a large amount, hypervitaminosis D is observed wherein blood calcium and phosphate increase to cause calcification in soft tissues such as kidney, artery, smooth muscle, and lung. The effective component of the present invention, i.e., vitamin D, active vitamin D and active vitamin D analogues is effective for prophylaxis and/or treatment of keratoconjunctivitis sicca even if it is administered in a small amount.

Accordingly, if it distributes to some extent into blood through eye mucosa, the side effects mentioned above would not be developed. Vitamin D, active vitamin D and active vitamin D analogues used in the present invention may be natural or artificial one. Examples of artificial active vitamin D analogues include α-calcidol (1α-monohydroxy vitamin D), 22-oxacalcitriol (OCT), calcipotriol (MC 903) and dihydrotachysterol.

The lacrimal fluid is amphiphilic and viscous. If the composition of the present invention is used in the form of eye drops, viscous media such as polysorbate, polyvinyl alcohol, methyl cellulose, sodium hyaluronate, chondroitin sulfuric acid, plant oils, and fats and oils are preferably used to prepare a viscous formulation so that the vitamin D's in the formulation can be retained on the surface of the eye balls for a long time to show a higher and longer effect for prophylaxis and/or treatment of keratoconjunctivitis sicca. Viscosity of the eye drops is preferably in the range of 0.01 to 10 poise.

EXAMPLES

The present invention will be explained more in detail with reference to Preparation Examples and Test Examples.

Preparation Example 1

Active vitamin D (22-oxacalcitriol)(1.0 mg/ml of ethanol) was diluted ten times with ethanol, followed by further diluting the solution 1000 times with a medium-chain fatty acid (triglyceride) to prepare a composition for prophylaxis and/or treatment of keratoconjunctivitis sicca having active vitamin D concentration of 0.1 μg/ml.

Preparation Example 2

Vitamin D (cholecalciferol)(50 mg/ml of ethanol) was diluted 100 times with ethanol, followed by further diluting the solution 100 times with an ophthalmic medium (an aqueous solution of 0.1% sodium hyaluronate (average molecular weight of about 1,800,000)) to prepare a composition for prophylaxis and/or treatment of keratoconjunctivitis sicca having vitamin D concentration of 5 μg/ml.

Preparation Example 3

Vitamin D (cholecalciferol)(50 mg/ml of ethanol) was diluted 100 times with ethanol, followed by further diluting the solution 100 times with an ophthalmic eye drop (a 0.1% Polysorbate 80 solution) to prepare a composition for prophylaxis and/or treatment of keratoconjunctivitis sicca having vitamin D concentration of 5 μg/ml.

Preparation Example 4

Active vitamin D (calcitriol, 1α,25-dihydroxy vitamin D)(1 mg/ml of ethanol) was diluted 10 times with ethanol, followed by further diluting the solution 1000 times with an ophthalmic eye drop (a 0.1% Polysorbate 80 solution) to prepare a composition for prophylaxis and/or treatment of keratoconjunctivitis sicca having active vitamin D concentration of 0.1 μg/ml.

Test Example 1

This test was conducted to examine the effect of active vitamin D on keratoconjunctivitis sicca.

Six Splague-Doly rats (3 weeks old) were used. All the rats were fed with vitamin A deficient feed for four weeks to cause keratoconjunctivitis sicca. From the beginning of the fifth week, three rats constituted Group D to which the composition for prophylaxis and/or treatment of keratoconjunctivitis sicca prepared in Preparation Example 4 was administered by dropping in the eyes while feeding the vitamin A deficient feed, and the other three rats constituted control Group C to which an ophthalmic eye drop (a 0.1% Polysorbate 80 solution) not containing active vitamin D was administered by dropping in the eyes while feeding the vitamin A deficient feed. The dropping was performed by dispensing 20 μl of the eye drops with a pipette and then dropping one or two drops in the eyes at a time. The dropping was conducted three times a day for both eyes. Two weeks after the dropping, the eyes were stained with sodium fluorescein to visualize the deflects in corneal epithelium and observed under a slit-lamp microscope. There were not observed superficial punctate keratitis in Group D but observed a slight spot-like staining in each of the eyes in Group C, in particular within the circle of about 2 mm diameter in the center of cornea. The observation under the slit-lamp microscope showed that the degree of inflammation associated with superficial punctate keratitis was much lower in the Group D rats than in the Group C rats. The Group C rats were more depressed and lower in excretion than the Group D rats. The test was completed five weeks after the initiation of the vitamin D deficient feeding.

In conclusion, the composition of the present invention clearly shows the effect of prophylaxis and/or treatment of keratoconjunctivitis sicca and effectively protects cornea and conjunctiva. These results show that the eye drops of the present invention are also effective in human being and are not detrimental to human bodies.

Test Example 2

Materials and Methods

In this test, 18 rats (Jla:Wister, female, weighing 100 g, purchased from Nihon Ikagaku Zairyo Kenkyusho) were bred by feeding vitamin A deficient feed to induce corneal and conjunctival disorder like human keratoconjunctivitis sicca.

After three weeks breeding, the rats were divided into three groups of six rats and the administration of the compositions was started. A first group was administered with a composition prepared by diluting 20 times the composition of Preparation Example 4 with an ophthalmic eye drop (0.1% Polysorbate 80 ophthalmic solution), a second group with a composition prepared by diluting 20 times the composition of Preparation Example 1 with an ophthalmic eye drop (0.1% Polysorbate 80 ophthalmic solution), and a third control group with an ophthalmic eye drop (0.1% Polysorbate 80 ophthalmic solution) free of vitamin D.

The vitamin A deficient feed was continuously fed to the animals while the compositions were administered.

The compositions were administered three times a day for four weeks in an amount of 5 μl for both eyes. One, two and four weeks after the administration started, observation was made under a slit-lamp microscope (a photo-slit lamp (Model SC-1200), KOWA) to examine abnormal conditions such as superficial punctate keratitis, solid material deposition, corneal ulcer, subepithelial haze/opacity and neovascularization and to make photographic records.

Results

Four weeks after the administration started, in the control group, superficial punctate keratitis and solid material deposition were observed in all the rats, and heavy disorder such as subepithelial haze/opacity and corneal ulcer were often observed.

In contrast, in the first and the second groups to which active vitamin D was administered, the degree and frequency of the disorder in the anterior ocular region were lower than the third group (control) and there were not observed heavy corneal disorder, which demonstrates obvious differences from the control group.

INDUSTRIAL APPLICABILITY

The composition of the present invention which comprises, as an effective component, at least one member selected from the group consisting of vitamin D, active vitamin D, and active vitamin D analogues can be administered locally in the eyes to prevent and/or treat keratoconjunctivitis sicca. A higher effect is expected if the composition is formulated in an aqueous solution similar to the lacrimal fluid such as an aqueous solution of sodium hyaluronate.

What is claimed is:

1. An ophthalmic composition for prophylaxis and/or treatment of keratoconjunctivitis sicca, which is locally administered to the eyes and which comprises, as an effective component, at least one member selected from the group consisting of vitamin D, active vitamin D, and active vitamin D analogues.

2. The ophthalmic composition for prophylaxis and/or treatment of keratoconjunctivitis sicca of claim 1 wherein the composition is in the form of eye drops.

3. The ophthalmic composition for prophylaxis and/or treatment of keratoconjunctivitis sicca of claim 1 wherein the effective component is at least one member selected from the group consisting of ergocalciferols, cholecalciferols, calcitriol, 1α,24- dihydroxy vitamin D, α-calcidol, calcifedol, 1α, 24, 25 -trihydroxy vitamin D, 1β, 25- dihydroxy vitamin D, 22-oxacalcitriol, calcipotriol and dihydrotachysterol.

4. The ophthalmic composition for prophylaxis and/or treatment of keratoconjunctivitis sicca of claim 1 wherein the effective component is 22-oxacalcitriol.

* * * * *